United States Patent [19]

Kaya et al.

[11] Patent Number: 4,766,553
[45] Date of Patent: Aug. 23, 1988

[54] HEAT EXCHANGER PERFORMANCE MONITOR

[76] Inventors: Azmi Kaya, 2365 Woodpark Rd., Akron, 44313; Marion A. Keyes, IV, 120 Riverstone Dr., Chagrin Falls, 44022, both of Ohio

[21] Appl. No.: 15,554

[22] Filed: Feb. 13, 1987

Related U.S. Application Data

[63] Continuation of Ser. No. 592,498, Mar. 23, 1984, abandoned.

[51] Int. Cl.$^4$ .................... G06F 15/20; G05D 23/00
[52] U.S. Cl. .................... 364/506; 165/11.1; 236/94; 364/550
[58] Field of Search ............... 364/506, 507, 550, 551, 364/557; 165/11.1, 39, 40, 95; 236/94; 374/165, 170; 73/170

[56] References Cited

U.S. PATENT DOCUMENTS

| | | | |
|---|---|---|---|
| 4,146,085 | 3/1979 | Wills | 236/94 X |
| 4,217,761 | 8/1980 | Cornaire et al. | 165/11 R X |
| 4,325,223 | 4/1982 | Cantley | 364/551 X |
| 4,390,058 | 6/1983 | Otake et al. | 165/11 R X |
| 4,463,571 | 8/1984 | Wiggs | 236/94 X |
| 4,615,302 | 10/1986 | Wynnyckyi et al. | 122/504.2 X |
| 4,671,952 | 6/1987 | Masse | 219/10.55 M X |

Primary Examiner—Parshotam S. Lall
Assistant Examiner—Joseph L. Dixon

[57] ABSTRACT

A performance monitor generates a fouling factor which indicates the level of fouling of a heat exchanger having a heat exchange surface area and through which a heat exchange medium passes having a known specific heat. Temperature transmitters are utilized to obtain values for the input and output temperatures of the heat exchange medium as well as the temperature in the heat exchanger of a heat exchange fluid used to transfer heat to or from the heat exchange medium. Modules are used to generate a value for an actual heat transfer coefficient in the heat exchanger as a function of the temperatures, flow rate and constant parameters such as area and specific heat, for the heat exchanger. The actual heat transfer coefficient is compared with a nominal or original heat transfer coefficient to determine if any deterioration in the coefficients has occurred which reflects the fouling of the heat exchanger. A simple ratio of the nominal to actual heat transfer coefficient is taken as a measure of this fouling factor.

9 Claims, 5 Drawing Sheets

4,766,553

HEAT EXCHANGER PERFORMANCE MONITOR

CROSS REFERENCE TO RELATED APPLICATION

This application is a continuation of application Ser. No. 592,498, filed Mar. 23, 1984, now abandoned.

FIELD AND BACKGROUND OF THE INVENTION

The present invention relates in general to heat exchangers and in particular to a new and useful monitor which is capable of determining the level of performance of a heat exchanger and specifically the amount of fouling on surfaces of the heat exchanger.

The performance of heat exchangers can be monitored. Such monitoring however, requires extensive calculations which, hitherto have been done using computers and high level programming languages. Such performance calculations have been disclosed in "Trouble-Shooting Compression Refrigeration Systems" by K. J. Vargas, *Chem. Engineering*, Mar. 22, 1982.

In order to determine the performance capacity of a heat exchanger under various operating conditions, deviations of the heat exchanger from design conditions must be accounted for by these extended calculations.

Experimental data has also been used to determine heat exchanger performance as disclosed in "Controlling Chiller Tube Fouling" by G. Leitner, *ASHRAE Journal*, February 1980. Such experimental data are not always available however.

Currently, computers are employed to determine the performance of heat exchangers in a prompt manner. The continuous availability of performance measurements helps in diagnosing several problems as they occur. Computers however, require high level language and highly trained personnel. This results in high costs for monitoring the heat exchangers.

SUMMARY OF THE INVENTION

The present inventon provides a monitoring system which has equivalent performance to prior art computer monitoring systems while costing less and being faster in operation. Essentially the advantages of an analog device as well as a computer are combined in the present invention.

The invention comprises a plurality of individual function blocks which are structured and assembled to perform the same operations as a high cost computer.

The invention is applicable to heat exchangers such as pre-coolers, air coolers, evaporators and condensers, and also to other devices having heat transfer surfaces such as boilers, for the purpose of determining fouling and slagging. The monitoring system of the invention can be used for example, to determine when a soot blowing operation should be commenced in a boiler.

Accordingly, an object of the invention is to provide a performance monitor for generating a fouling factor of a heat exchanger having a heat exchange surface area against one side of which a heat exchange medium passes, the medium having a specific heat, comprising first temperature transmitter means for supplying a signal corresponding to output temperature of the medium from the heat exchanger, second temperature transmitter means for supplying a signal corresponding to an input temperature of the medium to the heat exchanger, third temperature transmitter means for supplying a signal corresponding to a temperature of the heat exchanger on an opposite side of the heat exchange surface area and flow mass rate means for supplying a signal corresponding to the mass flow rate through the heat exchanger.

An actual heat transfer module is connected to the temperature transmitter means and the rate means for calculating an actual heat transfer coefficient as a function of the temperatures, mass flow rate, heat exchanger surface area and specific heat of the heat exchange medium. The performance monitor also includes a nominal heat transfer coefficient mechanism which supplies a signal corresponding to the nominal or original heat transfer coefficient of the heat exchanger. A divider is connected to the nominal heat transfer coefficient mechanism and the actual heat transfer module for dividing the nominal value by the actual value to obtain the fouling factor.

A further object of the present invention is to provide a performance monitor which utilizes a plurality of modules each including simple calculating units for obtaining a calculated value for the actual heat transfer coefficient and also a theoretical value for the nominal or original heat transfer coefficient value.

A still further object of the invention is to provide a heat exchanger performance monitor which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

The drawings illustrate one embodiment of a performance monitor which is particularly useful in monitoring the extent of fouling in a heat exchanger and, in particular, an evaporator.

As noted above, one of the reasons for degraded performance of a heat exchanger is fouling. There are other reasons, such as lack of flow, which may reduce the heat transfer capability. The present invention, however, isolates the effects of velocity to single out fouling as the cause of degraded heat transfer. The Heat Transfer equation is:

$$q = U \cdot A \cdot \Delta T_m \quad (1)$$

where;
q = Heat flow (Btu/hr)
U = Overall heat transfer coeff. (Btu/hr-ft²-F),
A = Surface area (ft²), and
$\Delta T_m$ = Logarithmic mean temperature difference.

The measured (actual) value of $U_{act}$ is compared with its normal value to determine the extent of fouling. The actual value is found from measurements as:

$$U_{act} = q/(A \cdot \Delta T_m) \quad (2)$$

Where each value on the right side of equation (2) is measured or known.

In general, two different fluids (such as water and refrigerant) exchange heat. The change in mean temperature, $\Delta T_m$ is written as a function of $T_{hot}$ = medium input, $T_{cold}$ = medium output, $T'_{cold}$ = refrigerant (or heat transfer fluid) input and $T'_{hot}$ = refrigerant output. The function is:

$$\Delta T_m = \frac{(T_{hot} - T'_{cold}) - (T_{cold} - T'_{hot})}{\ln\left(\frac{T_{hot} - T'_{cold}}{T_{cold} - T'_{hot}}\right)} \quad (3)$$

Figure 1:
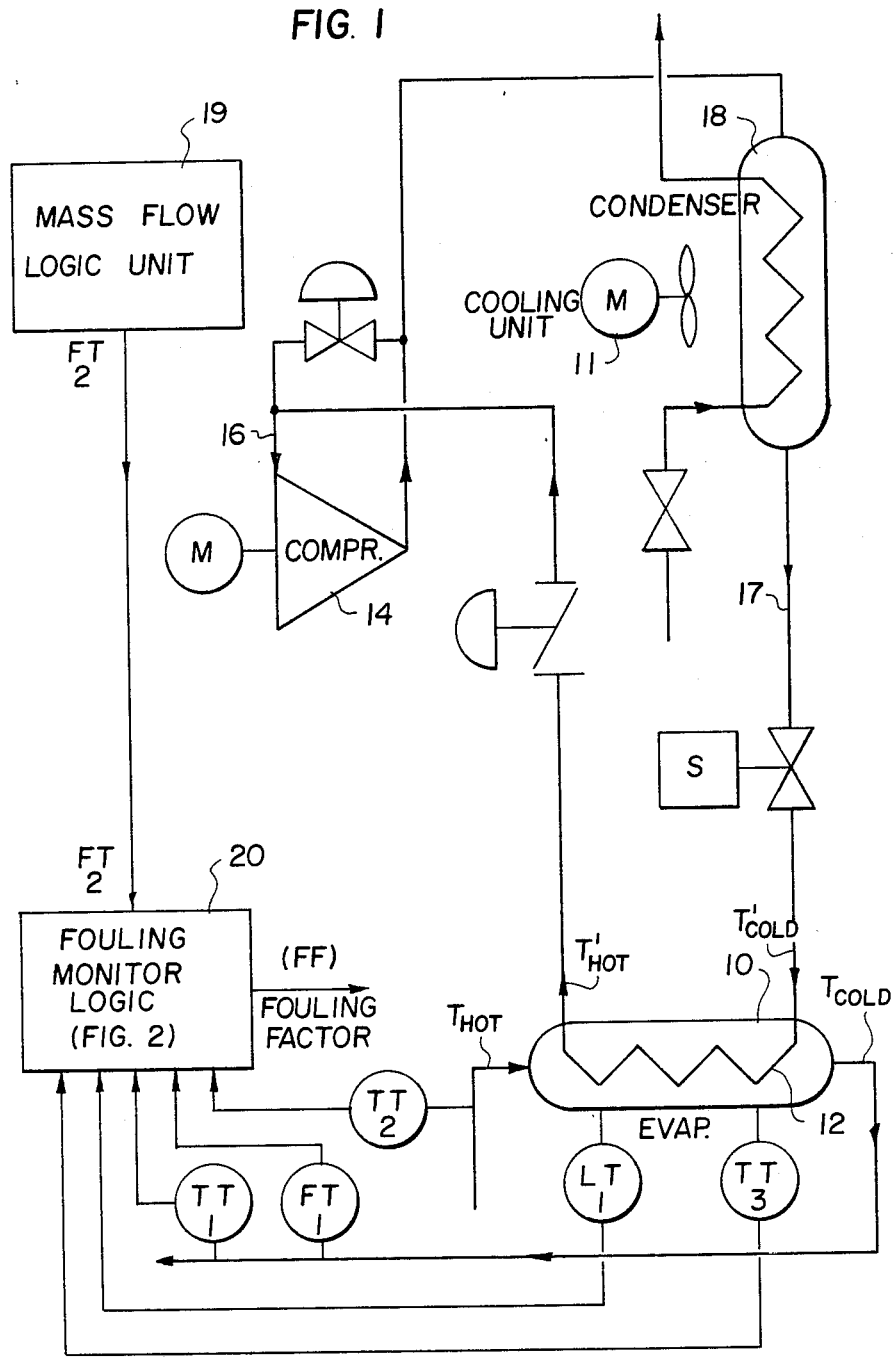
FIG. 1 is a schematic block diagram showing an evaporator as an example of a heat exchanger in combination with the performance monitor of the present invention.

As shown in FIG. 1, T refers to chilled water temperature T' to refrigerant or fluid temperature where the heat exchanger is an evaporator and where water is the medium. T' may be constant and still equation (3) applies. The value of q can be measured as the heat picked up by the water. The q value is found from the measurements of $T_{cold}$, $T_{hot}$ and mass flow rate $M_w$ as:

$$q = C_p M_w (T_{hot} - T_{cold}) \quad (4)$$

where, $C_p$ = specific heat of water which is known. The area of the heat exchanger is known as well.

The actual value of the heat exchanger coefficient ($U_{act}$) is found from the measurements by combining equation (2) and (4). The original or nominal value ($U_{ava}$) of the heat transfer coefficient is found by calculating a given fluid velocity and temperature conditions. ASHRAE Guide Books give the relation for calculating U values. For an evaporator with chilled water inside the tubes U is:

$$U = \frac{1}{\frac{1}{\phi_r h_r} + \frac{X}{K}\frac{A_o}{A_m} + \frac{A_o}{A_i}\left(\frac{1}{h_w} + r_f\right)} \quad (5)$$

where;
$\phi_r$ = fin shape factor,
$h_w$, $h_r$ = film coefficients for water and refrigerant,
X = wall thickness,
K = thermal conductivity of the tube material,
$A_m$ = mean area,
$A_o$, $A_i$ = outside and inside areas, and
$r_f$ = fouling factor.

In case $U_{ava}$ is provided by the manufacturer of the evaporator, equation (5) should be checked against the manufacturer's value and should be corrected by a multiplication factor $K_f$ if needed.

The values of $h_r$, $h_w$ are velocity and temperature dependent and the K value may be temperature dependent. Therefore, these values should be calculated, and U should be updated in order to compare it with the experimental data.

A general formula for the h (film coeff.) value is given by:

$$h = C\frac{K}{d}\left(\frac{Md}{\mu}\right)^n \left(\frac{\mu C_p}{K}\right)^m \quad (6)$$

where;
d = tube diameter
K = thermal conductivity of the fluid,
M = mass velocity (lb/(sec-ft²)),
$\mu$ = viscosity, and
m, n, C = constants.

The values of m, n, C depend upon the application or type of heat exchanger. Although the form of equation (6) may differ in special cases such as viscous fluids, the same terms are used.

In the following development of U, $h_w$ and $h_r$ are treated as general monlinear functions of temperature and velocity. The corrections on nominal values of $h_r^o$ and $h_w^o$, due to the variations of the temperature and the velocity, are made.

The case of Evaporator Monitor, as illustrated in FIGS. 1 to 6, will now be treated. The invention is applied to a flooded evaporator 10 with water inside the tubes shown schematically at 12. The refrigerator velocity will be small as compared with the other types of evaporators. However, mass velocity of refrigerant can be taken from measurements of compressor inlet flow at the inlet 16 of compressor 14 or it can directly be measured from the condenser outlet 17 of condenser 18. Here the compressor measurements at its inlet 16 are utilized.

Figure 2:
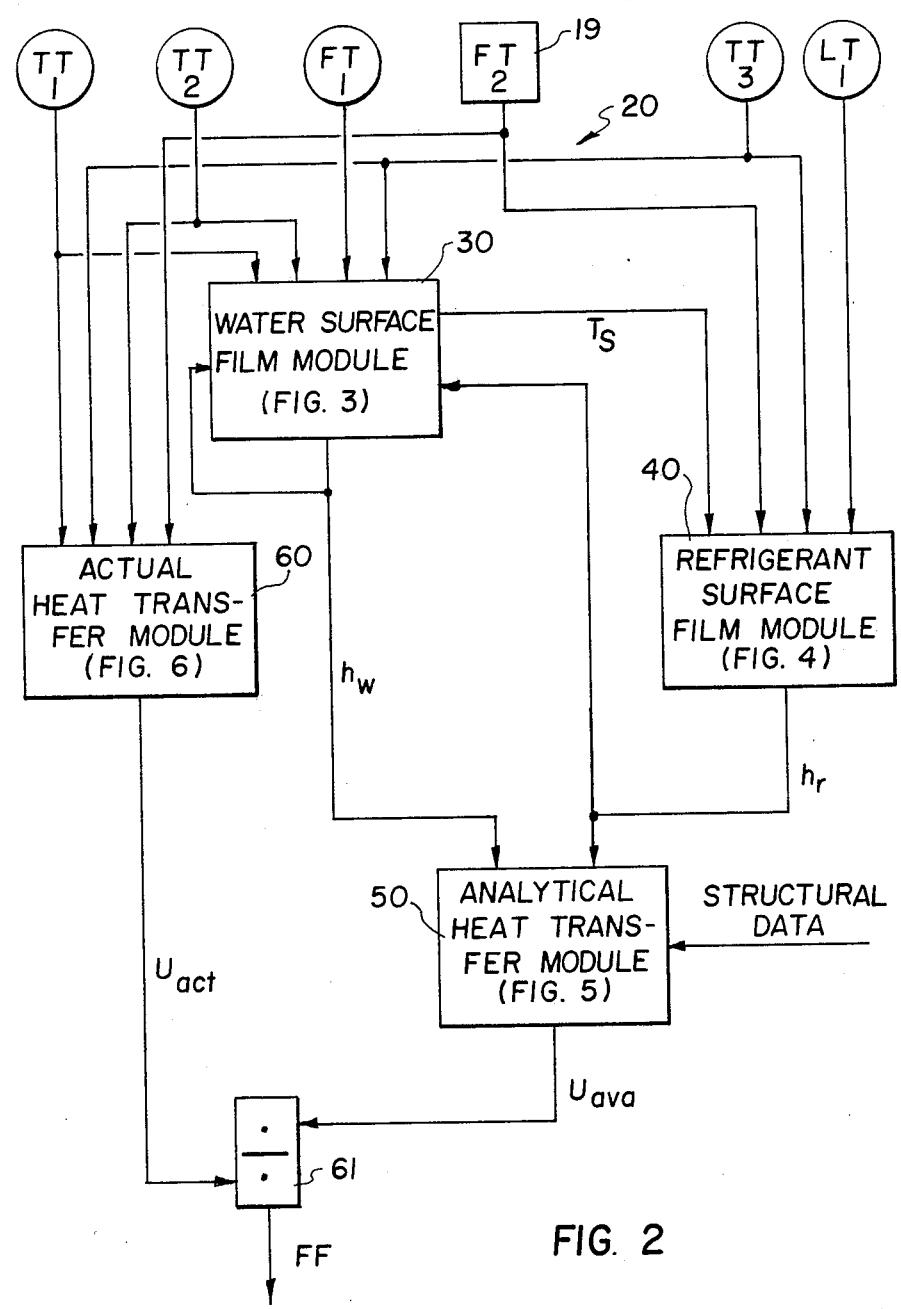
FIG. 2 is a block diagram showing the fouling monitor logic of FIG. 1 for generating a signal corresponding to a fouling factor of the heat exchanger.
Figure 3:
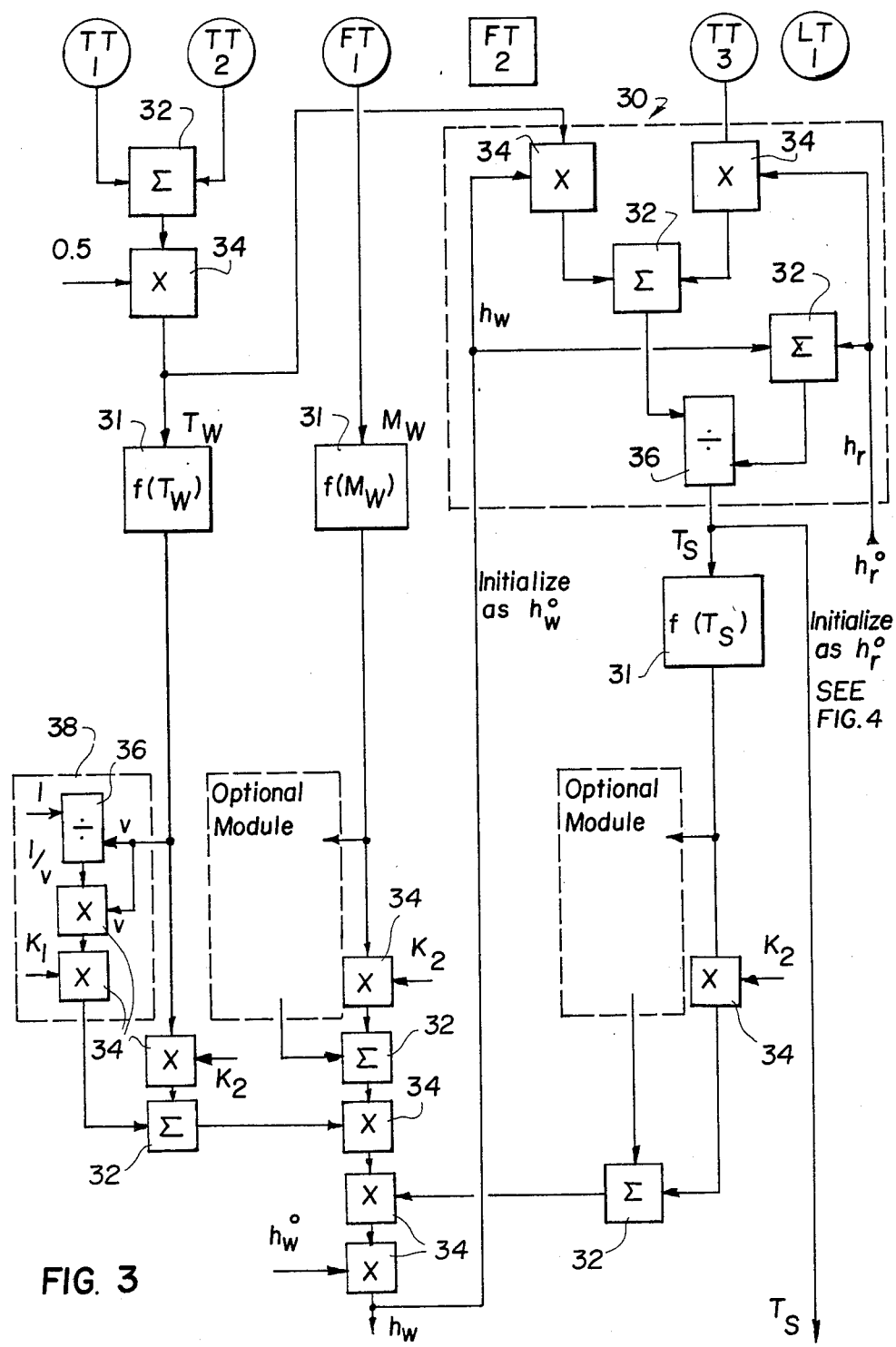
FIG. 3 is a block diagram showing the water surface film module used in the circuit of FIG. 2.
Figure 4:
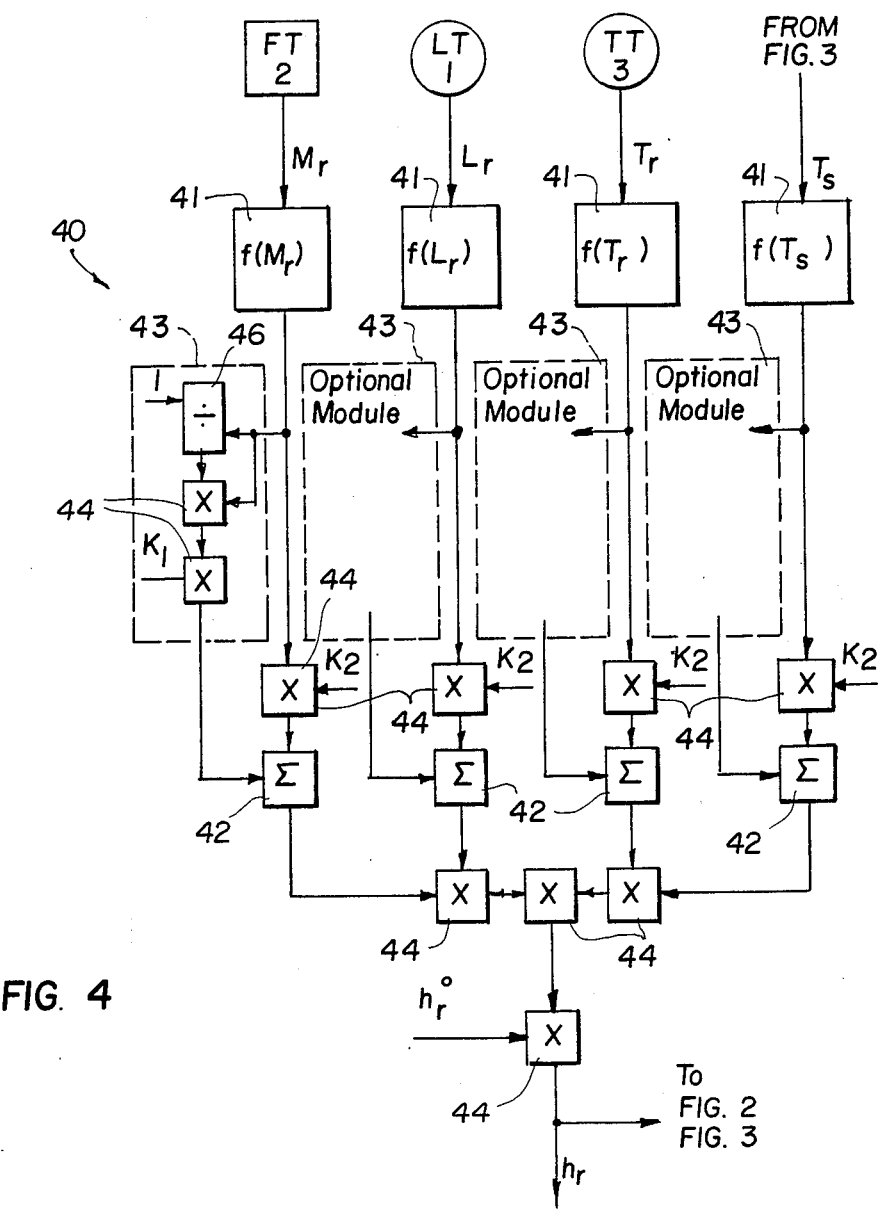
FIG. 4 is a block diagram showing the refrigerant surface film module used in the circuit of FIG. 2.

The evaporator system used with the inventive Evaporator monitor is shown in FIG. 1. The fouling monitor logic is shown in FIG. 2 and includes four modules. Note that the values $h_w$ and $h_r$ are fed back into a Water Surface Film Module 20 (detailed in FIG. 3) to calculate the surface temperature of the tubes, Ts. Similarly, the Refrigerant Surface Film Module 40 is shown in FIG. 4. The values $h_w$ and $h_r$ are fed into an Analytical Heat Transfer Module 50 (FIG. 5) along with structural data to calculate the nominal or original value of heat transfer coefficient, $U_{ava}$, as in equation (5). The actual value of heat transfer coefficient, $U_{act}$ is determined in unit 60 of FIG. 6. Going back to FIG. 2, the fouling factor, FF, is determined as the ratio of actual and original values of U:

$$FF = \frac{U_{ava}}{U_{act}} \quad (7)$$

The value of FF gives an indication of the cleanliness of the heat transfer surfaces independent of the other variables.

This fouling monitor logic is general and applies to other exchangers. The structures of FIGS. 3 and 4 determine $h_w$ and $h_r$ from equation (6), respectively. In FIGS. 3 and 4, any of the optional modules 38, 43 can be energized to eliminate the effect of a particular variable by setting $K_1 = 1$ and $K_2 = 0$. Otherwise, the values are set at $K_1 = 0$ and $K_2 = 1$ to include the effect. The functions "f" in FIGS. 3 and 4 are generated by varying a particular variable in equation (6). The method of generating functions "f" is given below. The relations for $h_w$ and $h_r$ in several heat exchanger applications are given in the ASHRAE Guide Books.

Consider $h_w$, given in equation (6) a nonlinear function of temperature and mass flow:

$$h_w = G(T_w, M_w, T_s) \quad (8)$$

where at nominal conditions;

$$h_w^\circ = G(T_w^\circ, M_w^\circ, T_s^\circ) \quad (9)$$

holds. Writing:

$$h_w = h_w^\circ \frac{h_w}{h_w^\circ} \quad (10)$$

where, $$\frac{h_w}{h_w^\circ} = \underbrace{\left[\frac{(h_w)^{T_w}}{h_w^\circ}\right]}_{f_1(T_w)} \underbrace{\left[\frac{(h_w)^{M_w}}{h_w^\circ}\right]}_{f_2(M_w)} \underbrace{\left[\frac{(h_w)^{T_s}}{h_w^\circ}\right]}_{f_3(T_s)} \quad (11)$$

The value of the numerator $f_1(T_w)$ is determined from equation (6) by calculating $h_w$ for various $T_w$ values while the other variables are held at their nominal values $M_w^\circ$ and $T_s^\circ$. The functions "f" are used in FIGS. 3 and 4.

Water cooled condensers and precoolers can also be monitored in the same way as the evaporator according to the invention. The heat transfer q can either be calculated by measuring condenser water parameters and using equation (4) or using the refrigerant side measurements. In that case the q value for a condenser is written as:

$$q = M_r(h_{gas} - h_{liq}) \quad (12)$$

where;
$M_r$ = refrigerant mass flow rate (lb/hr),
$h_{gas}$ = enthalpy of refrigerant entering, and
$h_{liq}$ = enthalpy of refrigerant leaving.

For evaporative and air-cooled condensers it is better to use equation (12) for q. For air-cooled condenser, water is replaced by air and the same equations apply. $\Delta T_m$ is calculated similarly.

For evaporative condensers, there is an intermediate fluid water between refrigerant and air. Determining $U_{act}$ is identical to the other cases. As $\Delta T_m$, the average value of $\Delta T_m$ for refrigerant to water and $\Delta T_m$ for refrigerant to air is used.

For analytical heat transfer coefficient, three surface film coefficients have to be calculated. Their calculations are covered in equation (6). A modified relation over equation (5) is:

$$U = \frac{1}{\frac{1}{\phi_r h_r} + \frac{X}{K}\frac{A_o}{A_m} + \frac{A_o}{A_i}\left(\frac{1}{h_w} + \frac{1}{h_a} + r_f\right)} \quad (13)$$

where;
$h_a$ = film coefficient for air.
To avoid undue complication, manufacturer's data should be used if possible. The functional relations as in equation (10) can be developed from the manufacturer's data in case the analytical calculations become impractical.

In greater detail, as shown in FIG. 1, three temperature transmitters $TT_1$, $TT_2$ and $TT_3$ are associated with the evaporator 10. Temperature transmitter $TT_1$ measures the output temperature of medium, in this case cold water which has temperature $T_{cold}$. Transmitter $TT_2$ measures the input temperature of the water at $T_{hot}$. Temperature transmitter $TT_3$ is used to measure the mean temperature in the evaporator. A single temperature value is used therefore for refrigerant input and output temperature in equation (3). Added accuracy can be obtained by using different temperature transmitters for the input and output temperature of the refrigerant or other heat exchange fluid in another heat exchanger environment.

The flow $FT_2$ of refrigerant through the evaporator is obtained from mass flow logic 19 at compressor inlet 16 of compressor 14 which is of known structure. $FT_2$ is applied to fouling monitor logic 20.

The level of refrigerant in the evaporator is measured by level transmitter $LT_1$. This value is used in obtaining the original or nominal heat transfer coefficient value in the circuitry of FIG. 4.

The mass flow rate of heat exchange medium is measured by flow transmitter $FT_1$.

The refrigerant is supplied through the evaporator 10 by compressor 14 in the refrigerant circuit. Controllable valves are shown which are of known structure.

The refrigerant is supplied through condenser 18 which is also cooled by a cooling unit 11, also of known design.

FIG. 2 shows the fouling monitor logic 20 which forms the performance monitor of the invention.

Actual heat transfer module 60 is connected to temperature transmitters $TT_1$, $TT_2$ and $TT_3$, as well as mass flow logic unit 19. As shown in greater detail in FIG. 6, module 60 generates a value corresponding to the actual heat transfer coefficient $U_{act}$.

Figure 5:
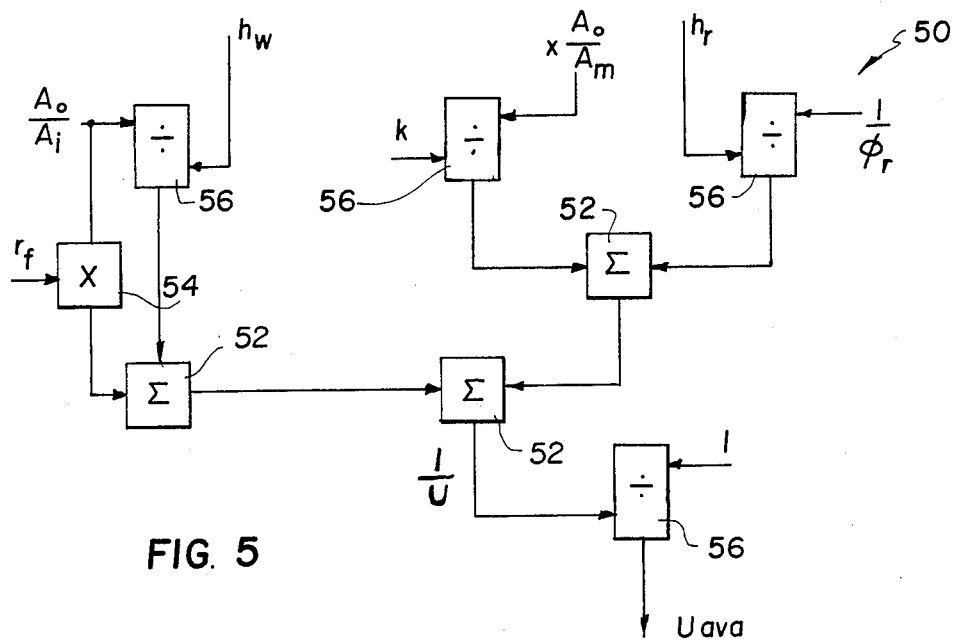
FIG. 5 is a block diagram of the analytical heat transfer module used in the circuit of FIG. 2.

The original or nominal heat transfer coefficient $U_{ava}$ can be used as a known value or can be ascertained using the three modules 30, 40 and 50 shown in FIG. 2 and detailed in FIGS. 3, 4, and 5 respectively.

The nominal or original heat transfer coefficient $U_{ava}$ is divided by the actual value, $U_{act}$, in a first divider unit 61 to generate the fouling factor FF as described in Equation (7).

FIG. 3 shows the water surface film module 30 which uses simple functional units such as summing units 32, multiplication units 34 and a second dividing unit 36, as well as additional somewhat more complicated units, to generate values $h_w$ and $T_s$ from Equation (6) by the use of Equation (6) and Equations (8) through (11). Optional modules 38 can be used to eliminate the effects of $T_w$, $M_w$, $T_s$.

Function generators 31 are utilized to generate more complex functions but are also of modular design. These function generators are utilized to generate the functions needed in Equation (11).

FIG. 4 illustrates the refrigerant surface film module 40 for calculating $h_r$. Here again, function generators 41 are utilized for generating the various functions needed for example in equation (11), as well as multipliers 44 and summing units 42. The Optional Modules 43 which are similar to the modules 38 of FIG. 3 are also provided.

FIG. 5 illustrates an analytical heat transfer module 50 which is connected to the water surface film module 30 and refrigerant surface film module 40, and is also made up of simple functional units such as summing units 52, a multiplier 54 and divider units 56. Module 50 implements Equation (5) to calculate the nominal or original heat transfer coefficient $U_{ava}$ as a function of $h_w$, and $h_r$, supplied from units 30 and 40 respectively. The structural data as described in Equation (5) are also utilized.

Figure 6:
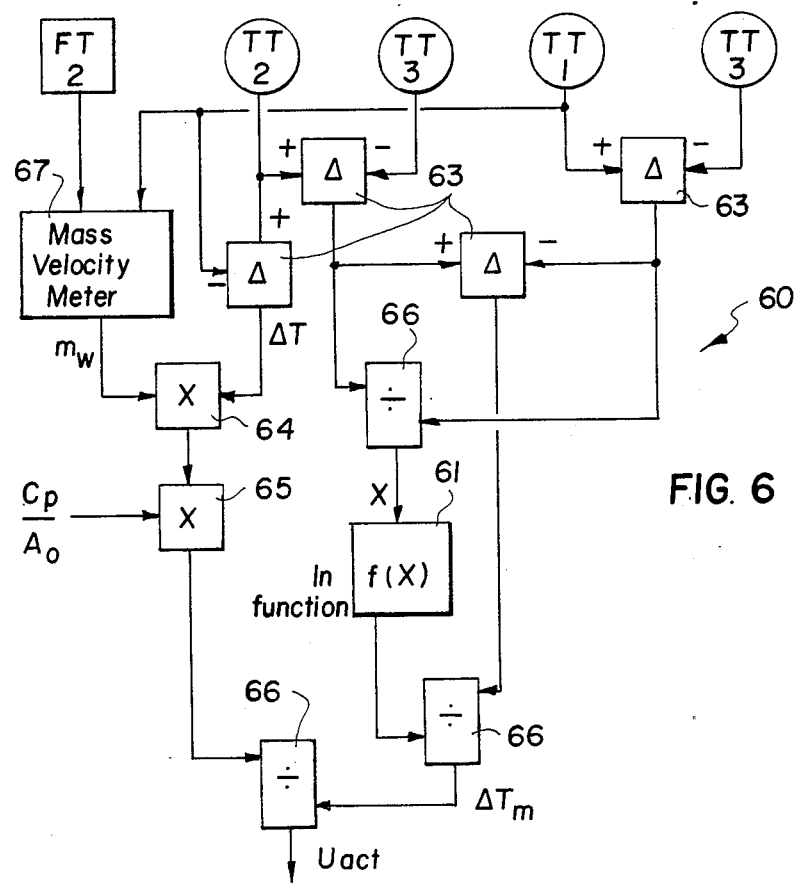
FIG. 6 is a block diagram of the actual heat transfer module used in the circuit of FIG. 2.

FIG. 6 illustrates the actual heat transfer module 60 which is used to run through equations (2), (3), and (4) for calculating the actual heat transfer coefficient $U_{act}$. Difference units 63 obtain the various differences between temperatures as supplied by the temperature transmitters $TT_1$, $TT_2$ and $TT_3$. A mass flow meter 67 (of known structure) supplies the mass flow rate $M_w$ to a multiplier 64 which, in multiplier 65 is multiplied by the ratio of the specific heat for the medium (in this case water) and the surface area of the heat exchange surface. Divider 66 is used in conjunction with the difference units to obtain the ratio whose natural logarithm ln is taken in function unit 61. Further dividers 66 are used to ultimately generate the $U_{act}$ value, according to the following equation derived by directly substituting equations (3) and (4) into equation (2):

$$U_{act} = \frac{q}{A \cdot \Delta T_m}$$
$$= \frac{C_p M_w (T_{hot} - T_{cold})}{A \cdot \left[ \frac{(T_{hot} - T'_{cold}) - (T_{cold} - T'_{hot})}{\ln\left( \frac{T_{hot} - T'_{cold}}{T_{cold} - T'_{hot}} \right)} \right]}$$

Since a single temperature is used for refrigerant input and output temperatures (i.e., $T'_{hot}$ and $T'_{cold}$) in equation (3), let $T'_{hot} = T'_{cold} = T_r$. Simplifying yields:

$$U_{act} = \frac{C_p M_w (T_{hot} - T_{cold})}{A [(T_{hot} - T_r) - (T_{cold} - T_r)]} \ln\left( \frac{T_{hot} - T_r}{T_{cold} - T_r} \right)$$

$$U_{act} = \frac{C_p M_w (T_{hot} - T_{cold})}{A [(T_{hot} - T_{cold}) - (T_r + T_r)]} \ln\left( \frac{T_{hot} - T_r}{T_{cold} - T_r} \right)$$

$$U_{act} = \frac{C_p M_w}{A} \ln\left( \frac{T_{hot} - T_r}{T_{hot} - T_r} \right)$$

It is noted that the various modules and compartmentalized function and simple mathematic operation blocks can all be provided by a NETWORK 90 instrument. NETWORK 90 is a trademark of the Bailey Controls Company of McDermott Incorporated. The use of such a modular arrangement avoids the use of a computer with its associated high level programming language to achieve the same purpose. The monitoring purpose is also achieved more rapidly.

While a specific embodiment of the invention has been shown and described in detail to illustrate the application of the principles of the invention, it will be understood that the invention may be embodied otherwise without departing from such principles.

What is claimed is:

1. A heat exchanger performance monitor for generating a fouling factor, indicative of the cleanliness of a heat exchanger, said heat exchanger having a heat exchange surface area for transferring heat between a medium which passes against one side of said heat exchange surface area and a heat exchange fluid which passes against an opposite side of said heat exchange surface area, comprising:

first temperature transmitter means for supplying a first signal corresponding to the output temperature of the medium exiting from the heat exchanger;

second temperature transmitter means for supplying a second signal corresponding to the input temperature of the medium entering the heat exchanger;

third temperature transmitter means for supplying a third signal corresponding to the temperature of the heat exchange fluid on the opposite side of the heat exchange surface area;

first mass flow rate means for supplying a fourth signal corresponding to the mass flow rate of medium passing through the heat exchanger;

second mass flow rate means for supplying a fifth signal corresponding to the mass flow rate of heat exchange fluid passing through the heat exchanger;

an actual heat transfer module, connected to said first, second and third temperature transmitter means and to said second mass flow rate means, for calculating a sixth signal corresponding to an actual heat transfer coefficient ($U_{act}$) of said heat exchanger as a function of said first, second, third and fifth signals, said heat exchange surface area, and a specific heat value of said medium;

means for calculating a seventh signal corresponding to a nominal heat transfer coefficient ($U_{ava}$) of said heat exchanger; and a first divider unit, connected to said actual heat transfer module for calculating said sixth signal corresponding to said actual heat transfer coefficient ($U_{act}$) and to said means for calculating said seventh signal corresponding to said nominal heat transfer coefficient ($U_{ava}$) for calculating an eighth signal corresponding to a ratio of said nominal heat transfer coefficient ($U_{ava}$) to said actual heat transfer coefficient ($U_{act}$), said ratio corresponding to the fouling factor of said heat exchanger.

2. A heat exchanger performance monitor according to claim 1, wherein said means for calculating said seventh signal corresponding to said nominal heat transfer coefficient ($U_{ava}$) comprises:

a medium surface film module for calculating a film coefficient of the medium $h_w$ as a function of said first and second signals corresponding to the output and input temperatures of the medium exiting and entering the heat exchanger, said third signal corresponding to the temperature of the heat exchange fluid on the opposite side of the heat exchange surface area, said fourth signal corresponding to the mass flow rate of medium passing through the heat exchanger;

a heat exchange fluid surface film module for calculating a film coefficient for the heat exchange fluid $h_r$ as a function of said fifth signal corresponding to the mass flow rate of heat exchange fluid passing through the heat exchanger, said third signal corresponding to the temperature of the heat exchange fluid on the opposite side of the heat exchange surface area, a surface temperature of the tubes, $T_s$, in the heat exchanger, and a level of the heat exchange fluid in said heat exchanger; and an analytical heat transfer module, connected to said medium surface film module and to said heat exchange fluid surface film module, for calculating said seventh signal corresponding to the nominal heat transfer coefficient ($U_{ava}$) as a function of the film coefficient of the medium, $h_w$, the film coefficient of the heat exchange fluid, $h_r$, and structural data of the heat exchanger.

3. A heat exchanger performance monitor according to claim 1, wherein said actual heat transfer module comprises:

a first difference unit having a first output signal corresponding to the difference between said first signal and said third signal;

a second difference unit having a second output signal corresponding to the difference between said second signal and said third signal;

a third difference unit, connected to said first and second difference units, having a third output signal corresponding to the difference between said second and first output signals;

a first divider unit, connected to said first and second difference units, having a fourth output signal corresponding to the ratio of said second output signal to said first output signal;

a natural logarithm function generator, connected to said first divider unit, having a fifth output signal corresponding to the natural logarithm of said fourth output signal;

a second divider unit, connected to said natural logarithm function generator and to said third difference unit, having a sixth output signal corresponding to the ratio of said third output signal to said fifth output signal;

a fourth difference unit having a seventh output signal corresponding to the difference between said second signal and said first signal;

a first multiplier unit having an eighth output signal corresponding to the product of said fifth signal and said seventh output signal;

a second multiplier unit, connected to said first multiplier unit, having a ninth output signal corresponding to the product of said eighth output signal and the ratio of the specific heat of the medium to the heat exchange surface area; and a third divider unit, connected to said second multiplier unit and to said second divider unit, for calculating said sixth signal corresponding to the actual heat transfer coefficient ($U_{act}$) of the heat exchanger according to the relation:

$$U_{act} = \frac{C_p M_w}{A} \ln\left(\frac{T_{hot} - T_r}{T_{cold} - T_r}\right)$$

wherein $C_p$ is the specific heat of the medium, $M_w$ is the mass flow rate of the medium, $T_{hot}$ is the input temperature of the medium, $T_{cold}$ is the output temperature of the medium, A is the heat exchange surface area, and $T_r$ is the temperature of the heat exchange fluid on the opposite side of the heat exchange surface area.

4. A heat exchanger performance monitor according to claim 1 wherein said medium is water.

5. A heat exchanger performance monitor according to claim 1 wherein said heat exchange fluid is water.

6. A heat exchanger performance monitor according to claim 1 wherein said heat exchanger is a pre-cooler.

7. A heat exchanger performance monitor according to claim 1 wherein said heat exchanger is an air-cooler.

8. A heat exchanger performance monitor according to claim 1 wherein said heat exchanger is an evaporator.

9. A heat exchanger performance monitor according to claim 1 wherein said heat exchanger is a condenser.

* * * * *

UNITED STATES PATENT AND TRADEMARK OFFICE
CERTIFICATE OF CORRECTION

PATENT NO. : 4,766,553
DATED : August 23, 1988
INVENTOR(S) : Azmi Kaya and Marion A. Keyes, IV It is certified that error appears in the above-identified patent and that said Letters Patent are hereby corrected as shown below:

On the face of the patent, the ASSIGNEE should be listed as set forth below:

ASSIGNEE: THE BABCOCK & WILCOX COMPANY
NEW ORLEANS, LOUISIANA

Signed and Sealed this

Tenth Day of January, 1989

Attest:

DONALD J. QUIGG

*Attesting Officer*  *Commissioner of Patents and Trademarks*